United States Patent [19]

Mukohyama et al.

[11] Patent Number: 4,606,771

[45] Date of Patent: Aug. 19, 1986

[54] ENTERIC COATING LIQUID

[75] Inventors: Hideaki Mukohyama; Ryoichi Hiraoka; Shohachi Ushijima; Motoyasu Saito, all of Yatsushiro, Japan

[73] Assignee: Kohjin Co., Ltd., Minato, Japan

[21] Appl. No.: 645,728

[22] Filed: Aug. 30, 1984

[30] Foreign Application Priority Data

Aug. 31, 1983 [JP] Japan ................................. 58-157936

[51] Int. Cl.$^4$ ........................... A61K 9/36; C08L 1/08
[52] U.S. Cl. .................................... 106/170; 106/169; 106/178; 106/194; 427/3; 424/35; 514/781
[58] Field of Search .......................... 424/35; 514/781; 106/169, 170, 178, 194; 427/3

[56] References Cited

U.S. PATENT DOCUMENTS

| | | | |
|---|---|---|---|
| 3,347,689 | 10/1967 | Futami et al. | 106/194 |
| 3,940,384 | 2/1976 | Teng et al. | 106/170 |
| 4,385,078 | 5/1983 | Onda et al. | 427/3 |
| 4,502,888 | 3/1985 | Leng et al. | 106/170 |

*Primary Examiner*—Ronald W. Griffin
*Attorney, Agent, or Firm*—Armstrong, Nikaido, Marmelstein & Kubovcik

[57] ABSTRACT

An aqueous enteric coating liquid having a good dispersion stability and a good resistance to gastric juice comprising an alkali metal salt of an acid having a acid dissociation constant of at least 3 at 25° C. and a water-insoluble oxycarboxylic acid type cellulose derivative dispersed in water or a mixture of water and at most 20% by weight of a lower alcohol.

5 Claims, No Drawings

ENTERIC COATING LIQUID

BACKGROUND OF THE INVENTION

The present invention relates to an enteric coating liquid, and more particularly to an aqueous enteric coating liquid containing an oxycarboxylic acid type cellulose derivative and enteric coated pharmaceuticals prepared by using the enteric coating liquid.

Hitherto, an enteric coating liquid has been prepared generally by dissolving in an organic solvent a high molecular substance which is insoluble in water and gastric juice, but soluble in intestinal juice, and adding, as occasion demands, a plasticizer, a coloring agent, etc. to the solution. However, the enteric coating according to such a process is economically disadvantageous, because a large quantity of an organic solvent is required in the preparation of the coating liquid and also the recovery of the solvent is difficult. Further, the use of the large quantity of the solvent causes problems such as safety to workers and danger due to ignition in the preparation of the enteric coating liquid and the pharmaceutical preparation, and safety to patients due to residual solvent in pharmaceuticals.

In recent years, recognition of the necessity for making the enteric coating liquid an aqueous system, namely for adopting a process using water as a dispersing medium, arose, and various processes have been proposed. However, the materials used for enteric coating are generally high molecular compounds having carboxyl groups which are difficult to form into an aqueous solution, because they are solubilized in water only in the form a salt in an alkaline water as a characteristic required for the enteric coating use.

Accordingly, there is little process put to practical use despite many proposals for preparing aqueous enteric coating liquids of high molecular compounds having carboxyl groups. The only one process practically adopted is a process using an aqueous emulsion of a methyl methacrylate/methacrylic acid copolymer prepared by emulsion polymerization. However, the preparation of aqueous enteric coating liquids according to this process is based on emulsion polymerization of acrylic monomers and, therefore, there is a possibility that a polymerization initiator, monomers, etc. remain and they cause a problem in safety for pharmaceutical use.

In such circumstances, as a process for preparing a completely aqueous enteric coating liquid by using high molecular compounds having carboxyl groups, there are known a process disclosed in Japanese Unexamined Patent Publication (Tokkyo Kokai) No. 7116/1976 wherein a high molecular compound is converted into a water-soluble salt, an aqueous solution thereof is coated on solid pharmaceuticals and the coated pharmaceuticals are treated with an acid to convert the salt into the original acid type high molecular compound; and a process disclosed in Japanese Examined Patent Publication (Tokkyo Kokoku) No. 12614/1981 wherein a dispersion of an enteric cellulose derivative powder having a particle size of not more than 100 μm and a gelling agent having a boiling point of not less than 100° C. in water is used for enteric coating. However, the former process has the disadvantages in that it is not suitable for coating pharmaceuticals unstable to acids and also, because of difficulty in completely converting the coating layer into the acid type, the first fluid resistance of the coating film, namely a resistance to a simulated gastric fluid which is saline water adjusted to a pH about 1.2 with hydrochloric acid, is insufficient. The latter process has the disadvantage that coating using a gear pump is difficult because of poor dispersion stability, as well as a problem that since the high molecular compound per se has no film forming property and requires a large quantity of a gelling agent, use of a plasticizer is necessary and, accordingly, there is a possibility of insufficient first fluid resistance.

An object of the present invention is to provide an aqueous enteric coating liquid containing a water-insoluble oxycarboxylic acid type cellulose derivative as a main component and having a good dispersion stability and a good film forming property, namely first fluid resistance.

Another object of the invention is to provide enteric coated pharmaceuticals covered with a continuous film formed from an aqueous coating liquid containing a water-insoluble oxycarboxylic acid type cellulose derivative as a main component.

These and other objects of the present invention will become apparent from the description hereinafter.

SUMMARY OF THE INVENTION

The present inventors made a study on an economical, stable aqueous enteric coating liquid in order to solve the problems of the above-mentioned prior art, and have now found that a dispersion containing, as essential components, an alkali metal salt of an acid having an acid dissociation constant (pKa) of at least 3 at 25° C. and a water-insoluble oxycarboxylic acid type cellulose derivative dispersed in water or a mixture of water and at most 20% by weight of a lower alcohol having 1 to 3 carbon atoms is suitable for use in enteric coatings.

In accordance with the present invention, there is provided an enteric coating liquid comprising an alkali metal salt of an acid having an acid dissociation constant (pKa) of at least 3 at 25° C. and a water-insoluble oxycarboxylic acid type cellulose derivative dispersed in water or a mixture of water and at most 20% by weight of a lower alcohol having 1 to 3 carbon atoms.

A coating film obtained from a solution of the oxycarboxylic acid type cellulose derivative dissolved in a mere aqueous alkaline solution, e.g. an aqueous solution of a caustic alkali such as sodium hydroxide or potassium hydroxide or an aqueous solution of a volatile amine such as ammonia or methylamine has no practicality because of the first fluid resistance. In contrast thereto, surprisingly, an aqueous dispersion of the invention obtained by dispersing the oxycarboxylic acid type cellulose derivative in an aqueous solution of the alkali metal salt of an acid having pKa of at least 3 dissolved in water or a water-alcohol mixed solvent forms a film having a good first fluid resistance of the same level as that of a film obtained from conventional enteric coating liquids of an organic solvent type.

The term "first fluid resistance" as used herein means a resistance to a simulated gastric fluid, i.e. saline water adjusted to a pH of about 1.2 with hydrochloric acid, such that a coating film is not disintegrated, ruptured, peeled off or otherwise broken when immersed in the simulated gastric fluid.

DETAILED DESCRIPTION

The oxycarboxylic acid type cellulose derivatives used in the present invention are cellulose derivatives wherein at least a part of 3 hydroxyl groups per glucose unit skeleton of cellulose or a hydroxyalkyl cellulose wherein the alkyl is a $C_1$ to $C_5$ alkyl is replaced by a group selected from a carboxyalkyl ether group of the formula: $-OC_nH_{2n}COOH$ and a half ester group based on a dicarboxylic acid, e.g. phthalic, succinic, maleic, glutaric, tetrahydrophthalic and hexahydrophthalic acids, and by a group selected from an ether group of the formula: $-OC_nH_{2n+1}$ and an ester group of the formula:

provided that the alkyl is a $C_1$ to $C_5$ alkyl, n is an integer of 1 to 5, and R is an alkyl group having 1 to 5 carbon atoms or a higher fatty acid residue. e.g. a fatty acid residue having 11 to 17 carbon atoms. The oxycarboxylic acid type cellulose derivatives are classified into three groups, i.e. cellulose ether compounds, cellulose ester compounds and cellulose ether ester compounds. The term "ether group" or "ester group" as used herein means an atomic group introduced into cellulose unit through ester linkage or ether linkage. The ester group includes, for instance, ester groups derived from acetic acid, propionic acid, butyric acid, succinic acid, phthalic acid, and a higher fatty acid. The ether group includes, for instance, a carboxylalkyl ether group, an alkyl ether group and a hydroxyalkyl ether group, provided that the alkyl is a $C_1$ to $C_5$ alkyl. Oxycarboxylic acid type cellulose derivatives other than the derivatives defined above are insufficient in hydrophilic property and inferior in dispersibility in water and, therefore, are not suitable as a coating material for use in aqueous enteric coating liquid.

Examples of the oxycarboxylic acid type cellulose derivatives used in the present invention are, for instance, a carboxyalkyl-alkyl cellulose mixed ether compound such as carboxymethyl ethyl cellulose, carboxyethyl methyl cellulose, carboxybutyl ethyl cellulose or carboxypropyl methyl cellulose; a cellulose ether ester compound such as hydroxypropyl methyl cellulose succinate, hydroxypropyl methyl cellulose phthalate, acid succinyl-acid phthaloyl mixed ester of hydroxypropyl methyl cellulose or acid succinyl-propionyl mixed ester of hydroxypropyl methyl cellulose; and a cellulose mixed ester compound such as cellulose acetate phthalate or cellulose acetate succinate.

The oxycarboxylic acid type cellulose derivatives are not particularly limited with respect to the shape and size so long as they are in the form of powder, but a powder having a particle size of not more than 100 μm, especially not more than about 10 μm, is particularly preferred. The manner of preparing such a powder is not particularly limited, and mechanical pulverization and physicochemical pulverization can be suitably adopted.

The alkali metal salts of acids having an acid dissociation constant (pKa) of at least 3 at 25° C. used as another essential component in the present invention include alkali metal salts of monobasic acids such a acetic acid (pKa=4.76), lactic acid (pKa=3.86) and butyric acid (pKa=4.82); and alkali metal salts of various polybasic acids, e.g. alkali metal salts of dibasic acids such as succinic acid ($pKa_1=4.21$, $pKa_2=5.64$), d-tartaric acid ($pKa_1=3.04$, $pKa_2=4.37$), carbonic acid ($pKa_1=6.35$, $pKa_2=10.33$), fumaric acid ($pKa_1=3.02$, $pKa_2=4.38$) and malic acid ($pKa_1=3.46$, $pKa_2=5.05$); and alkali metal salts of tribasic acids such as citric acid ($pKa_1=3.13$, $pKa_2=4.76$, $pKa_3=6.40$). In case of a polybasic acid, it is sufficient that at least one of a plurality of acid dissociation constants is not less than 3, and for instance, alkali metal salts of malonic acid ($pKa_1=2.84$, $pKa_2=5.69$), maleic acid ($pKa_1=1.94$, $pKa_2=6.26$) and phosphoric acid ($pKa_1=2.15$, $pKa_2=7.20$, $pKa_3=12.4$) are examples of the alkali metal salts in the invention.

The alkali metal salt of an acid having a pKa of at least 3 has not only the effect of raising the dispersion stability of the oxycarboxylic acid type cellulose derivative into a dispersion medium, but also a plasticizing effect. Therefore, it contributes to film-formability, namely improvement in first fluid resistance of coating film. The amount of the alkali metal salt varies depending on the kind of the oxycarboxylic acid type cellulose derivative, the dosage form to be coated, etc., and is suitably determined so that the first fluid resistance of the oxycarboxylic acid type cellulose derivative film is not lowered. In general, the use of the alkali metal salt in an amount of not more than 30 % by weight based on the oxycarboxylic acid type cellulose derivative is sufficient. Preferably, the alkali metal salt is employed in an amount of one or higher percent by weight. The alkali metal salt may be formed in a dispersion medium by neutralization of a corresponding acid with a caustic alkali, instead of using the alkali metal salt.

The pH of the dispersion system varies depending on the kind and amount of the alkali metal salt used, but it is possible adjust the system to a suitable pH range according to the kind of medicine to be coated, if necessary, by further adding an acid or caustic alkali corresponding to the alkali metal salt unless agglomeration or dissolution of the cellulose derivative occurs. Since the alkali metal salt used in the invention has essentially a buffer action, the pH can be easily set by selecting an alkali metal salt of an acid having an acid dissociation constant (pKa) corresponding to the desired pH range. This is one aspect of the usefulness of the invention.

Although water is preferably employed as a dispersion medium, a lower alcohol having 1 to 3 carbon atoms can be added to water in an amount such that a dispersoid is not agglomerated in the dispersion medium. The use of the alcohol is effective for improving the drying efficiency in spray coating or improving the evenness of coating film. Preferably, the content of the alcohol in the water-alcohol dispersion medium is at most 20 % by weight..

The manner of dispersing the dispersoid into the dispersion medium is not particularly limited, and general mixing and dispersing methods are adoptable.

Various additives may be employed in the present invention, as occasion demands, for instance, an antifoaming agent such as silicon oil; an emulsifier for the purpose of improving the dispersion stability of the dispersoid; a film forming assistant for the purpose of improving the film forming property of coating liquid, e.g. a cellulose derivative such as methyl cellulose, hydroxyethyl cellulose, hydroxypropyl cellulose, hydroxypropyl methyl cellulose or carboxymethyl cellulose, a water-soluble synthetic polymer such as polyvinyl alcohol, polyvinyl pyrrolidone, sodium polyacrylate, polyethylene glycol or polyethylene oxide, and a natural gum such as carrageenan, guar gum, sodium alginate, gelatin or gum arabic; and a plasticizer for the purpose of improving the plasticity of coating film, e.g.

propylene glycol, various phthalic acid esters, various citric acid esters such as triethyl citrate, various tri-, di- or monoglycerides of lower and higher fatty acids, and natural oil and fats such as castor oil, olive oil and sesame oil. The additives may be added at the time of dispersing the dispersoid or after dispersing in an amount such that they do not impair the functions of the enteric coating material.

The primary object of the present invention is to provide an aqueous enteric coating liquid, and accordingly, as a matter of course, selection of the enteric coating material per se is an important factor to obtain better coating liquids. The following points can provide the criteria for selecting the enteric coating material.

(1) It is advantageous that the coating material per se is rich in hydrophilic property within the range of not impairing the enteric function.

(2) Since the coating liquid is made up into an aqueous system and submitted to coating, the higher the hydrolysis resistance of the coating material per se, the higher the practical value.

From the above point of view. oxycarboxylic acid type cellulose mixed ethers having high hydrophilic property and hydrolysis resistance, namely carboxyalkyl methyl celluloses and carboxylalkyl ethyl celluloses wherein the alkyl group is an alkyl group having 1 to 5 carbon atoms, are particularly preferred as an enteric coating material among the oxycarboxylic acid type cellulose derivatives defined before. Representative examples of the carboxyalkyl methy or ethyl cellulose are, for instance, carboxymethyl ethyl cellulose, carboxyethyl ethyl cellulose, carboxybutyl ethyl cellulose and carboxypropyl methyl cellulose.

The content of the oxycarboxylic acid type cellulose derivative in the enteric coating liquid of the invention is not particularly limited, but in practice, a range of about 5 to about 30% by weight is adequate in view mainly of the coating apparatus capacity.

Any known coating apparatuses such as pan coating apparatus, drum type coating apparatus and fluidized coating apparatus can be employed in coating the enteric coating liquid of the invention onto solid pharmaceuticals.

Since the minimum film-forming temperature (MFT) of the enteric coating liquid of the present invention is not so high and it forms a stable continuous film under a moderate drying condition, excellent enteric coated pharmaceuticals can be obtained by coating the surface or inner layer of solid medicine, tablet, multilayer tablet, granule or capsule with the enteric coating liquid, by incorporating the enteric coating material into a capsule materials, or by mixing a medicine with the enteric coating material upon the preparation of granule.

The present invention is more specifically described and explained by means of the following Examples in which all % and parts are by weight unless otherwise noted. It is to be understood that the present invention is not limited to the Examples, and various changes and modifications may be made in the invention without departing from the spirit and scope thereof.

In the Examples, the disintegration test of enteric coated pharmaceuticals was made by employing test fluids provided in Pharmacopedia of Japan (10th edition) as follows:

Test fluids (1) 1st fluid (simulated gastric fluid)

In 24.0 ml of diluted hydrochloric acid solution is dissolved 2.0 g of sodium chloride, and water is added to the solution to adjust the volume to 1,000 ml. This test fluid has a pH of about 1.2.

(2) 2nd fluid (simulated intestinal fluid)

To 250 ml of 0.2 M monobasic potassium phosphate is added 118 ml of 0.2 N sodium hydroxide, and the total volume is adjusted to 1,000 ml with water. This test fluid has a pH of about 6.8.

The test is made by immersing a sample in the 1st fluid for 120 minutes and observing whether an active substance in a coating film is leaked by disintegration of the sample or by rupture, peeling off or otherwise breaking of the coating film. In case that there is no evidence of disintegration, the sample is further immersed in the 2nd fluid, and the state of disintegration is observed.

EXAMPLE 1

To 81.5 parts of an aqueous solution of sodium lactate obtained by adding 1 part by volume of a 0.1 M aqueous solution of sodium hydroxide to 1 part by volume of a 0.1 M aqueous solution of lactic acid were added 0.05 part of polyoxyethylene sorbitan monooleate (commercial name "Tween 80" made by Kao Atlas Kabushiki Kaisha) and 5 parts of a 2% aqueous solution of hydroxypropyl methyl cellulose (commercial name "TC-5R" made by Shin-Etsu Chemical Co., Ltd.) to give a dispersion medium. To the dispersion medium was added 1 part of a fatty acid glyceryl ester (composed mainly of caprylic acid monoglyceride, commercial name "MGK" made by Nikko Chemicals Kabushiki Kaisha), which was dispersed by a homogenizer. To the dispersion was then gradually added 10 parts of carboxymethyl ethyl cellulose powder having an average particle size of 30 $\mu$m (degree of substitution for carboxymethyl group: 0.52, degree of substitution for ethoxy group: 1.95), and after thoroughly dispersing it, 27.45 parts of water was added and the powder was thoroughly dispersed by the homogenizer to give a white dispersion of carboxymethyl ethyl cellulose.

The minimum film-forming temperature (hereinafter referred to as "MFT") of the obtained dispersion was 37° C., and the dispersion formed a transparent, uniform and continuous film at temperatures of not less than MFT.

An automatic pan coating apparatus (Type FM-2 made by Freund Industry Co., Ltd.) was charged with 1 kg of tablets (each having a diameter of 8 mm and a weight of 150 mg) composed mainly of lactose and microcrystalline cellulose, and the above dispersion was coated onto the tablets in an amount of about 15 mg (as solids) per tablet.

The obtained enteric coated tablet was subjected to the disintegration test. No change was observed in the test with the first fluid, and disintegration was observed in 12 to 15 minutes in the test with the second fluid.

EXAMPLE 2

A white dispersion of carboxymethyl ethyl cellulose was prepared in the same manner as in Example 1 except that 81.5 parts of an aqueous solution of sodium tartrate obtained by adding 2 parts by volume of a 0.1 M aqueous solution of sodium hydroxide to 1 part by volume of a 0.1 M aqueous solution of tartaric acid was employed instead of the aqueous sodium lactate solution.

The dispersion had a MFT of 42° C., and formed a transparent, uniform and continuous film at temperatures of not less than MFT.

The dispersion was coated on tablets in the same manner as in Example 1, and the enteric coated tablet was subjected to the disintegration test. No change was observed in the test with the first fluid, and disintegration was observed in 12 to 14 minutes in the test with the second fluid.

EXAMPLE 3

A white dispersion of carboxymethyl ethyl cellulose was prepared in the same manner as in Example 1 except that 81.5 parts of an aqueous solution of sodium citrate obtained by adding 3 parts by volume of a 0.1 M aqueous solution of sodium hydroxide to 1 part by volume of a 0.1 M aqueous solution of citric acid was employed instead of the aqueous sodium lactate solution.

The dispersion had a MFT of 27° C., and formed a transparent uniform film at temperatures of not less than MFT.

The dispersion was coated on tablets in the same manner as in Example 1, and the enteric coated tablet was subjected to the disintegration test. No change was observed in the test with the first fluid, and disintegration was observed in 10 to 13 minutes in the test with the second fluid.

EXAMPLE 4

A dispersion medium was prepared by adding 0.05 part of polyoxyethylene sorbitan monooleate (commercial name "Tween 80" made by Kao Atlas Kabushiki Kaisha) and 5 parts of a 2% aqueous solution of polyvinyl alcohol (commercial name "Gohsenol NL-5" made by Nippon Gohsei Kagaku Kogyo Kabushiki Kaisha) to 81.5 parts of a 0.03 M aqueous solution of sodium citrate. To the dispersion medium was added 1 part of castor oil which was dispersed by a homogenizer. Then, 10 parts of the same carboxymethyl ethyl cellulose powder as used in Example 1 was gradually added to the dispersion medium and thoroughly dispersed. To the dispersion was added 27.45 parts of water containing 0.00163 part of silicon oil which was thoroughly dispersed by the homogenizer to give a white dispersion of carboxymethyl ethyl cellulose.

The dispersion had a MFT of 30° C., and formed a transparent, uniform and continuous film at temperatures of not less than MFT.

The dispersion was coated on tablets in the same manner as in Example 1, and the enteric coated tablet was subjected to the disintegration test. No change was observed in the test with the first fluid, and disintegration was observed in 10 to 14 minutes in the test with the second fluid.

EXAMPLE 5

A white dispersion of carboxyethyl ethyl cellulose was prepared in the same manner as in Example 3 except that carboxyethyl ethyl cellulose (degree of substitution for carboxyethyl group: 0.56, degree of substitution for ethoxy group: 1.81) was employed instead of carboxymethyl ethyl cellulose.

The dispersion had a MFT of 30° C., and formed a transparent uniform film at temperatures of not less than MFT. Enteric coated tablets were prepared employing the obtained dispersion in the same manner as in Example 1, and subjected to the disintegration test. No change was observed in the test with the first fluid, and disintegration was observed in 11 to 15 minutes in the test with the second fluid.

EXAMPLE 6

A white dispersion of hydroxypropyl methyl cellulose phthalate was prepared in the same manner as in Example 3 except that hydroxypropyl methyl cellulose phthalate powder having an average particle size of 30 μm (commercial name "HP-55" made by Shin-Etsu Chemical Co., Ltd.) was employed instead of carboxymethyl ethyl cellulose.

The dispersion had a MFT of 45° C., and formed a transparent uniform film at temperatures of not less than MFT. The coating of the dispersion was conducted in the same manner as in Example 1, and the obtained enteric coated tablet was subjected to the disintegration test. No change was observed in the test with the first fluid, and disintegration was observed in 14 to 16 minutes in the test with the second fluid.

EXAMPLE 7

Hydrous granules of carboxymethyl ethyl cellulose (degree of substitution for carboxymethyl group: 0.48, degree of substitution for ethoxy group: 2.01, viscosity of 5% solution in a mixed solvent of ethanol and water in a ratio of 80:20 by weight: 12.6 cP) were pulverized without drying to give a slurry of particles having an average particle size of 4 μm, and the slurry was dried to give a cake. An aqueous dispersion was prepared in the same manner as in Example 3 except that the thus obtained cake was employed. The obtained dispersion had a MFT of 27° C., and formed a transparent, uniform and continuous film at temperatures of not less than the MFT. At the time of dispersing the cellulose particles, there was no dusting and the dispersion was easily prepared.

An 8% aqueous solution of hydroxypropyl methyl cellulose (commercial name "TC-5R" made by Shin-Etsu Chemical Co., Ltd.) was coated on tablets (diameter: 8 mm, weight: about 200 mg per tablet) composed of microcrystalline cellulose powder (commercial name "Avicel" made by Asahi Kasei Kogyo Kabushiki Kaisha) and hydroxypropyl starch as rapid disintegrative vehicle (commercial name "Perfiller" made by Freund Industry Co., Ltd.) in a ratio of 1:1 by weight, in an amount of 2.5% based on the weight of tablet.

An automatic film coating apparatus (Type HCT-MINI made by Freund Industry Co., Ltd.) was charged with 0.35 kg of the coated tablets, and the above dispersion was sprayed at a rate of 5 ml/minute to coat the tablets in an amount of about 12% based on the weight of the original tablet and dried. The thus obtained enteric coated tablets were subjected to the disintegration test. No change was observed in the test with the first fluid, and disintegration was observed in 8 to 12 minutes in the test with the second fluid.

EXAMPLE 8

A white dispersion of carboxymethyl ethyl cellulose was prepared in the same manner as in Example 1 except that acetylated lard fatty acid monoglyceride (commercial name "Myvacet 9-40T" made by Eastman Kodak Company) was employed as a fatty acid glyceryl ester and a mixed solvent consisting of 5.45 parts of ethanol and 22 parts of water was added instead of 27.45 parts of water after dispersing carboxymethyl ethyl cellulose into a dispersion medium.

The obtained dispersion had a MFT of 33° C., and formed a transparent uniform film at temperatures of not less than the MFT. The dispersion was then coated on tablets in an amount of about 15 mg (as solids) per tablet by employing the same tablets and coating apparatus as used in Example 1. The enteric coated tablets were subjected to the disintegration test. No change was observed in the test with the first fluid, and disintegration was observed in 13 to 16 minutes in the test with the second fluid.

EXAMPLE 9

To 87.7 parts of water was gradually added 10 parts of carboxymethyl ethyl cellulose powder having an average particle size of 7.0 μm (degree of substitution for carboxymethyl group: 0.50, degree of substitution for ethoxy group: 2.00), which was thoroughly dispersed by a homogenizer. A dispersion consisting of 0.05 part of polyoxyethylene sorbitan monooleate (Tween 80 made by Kao Atlas Kabushiki Kaisha), 5.04 parts of a 2% aqueous solution of hydroxypropyl methyl cellulose (TC-5R made by Shin-Etsu Chemical Co., Ltd.), 0.034 part of citric acid, 0.594 part of sodium citrate and 3 parts of triethyl citrate was added to the carboxymethy ethyl cellulose dispersion with agitation and thoroughly agitated to give a white dispersion.

The dispersion had a MFT of 25° C., and formed a transparent uniform film at temperatures of not less than the MFT. The coating of the dispersion was conducted in the same manner as in Example 1, and the obtained enteric coated tablets were subjected to the disintegration test. No change was observed in the test with the first fluid, and disintegration was observed in 10 to 12 minutes in the test with the second fluid.

COMPARATIVE EXAMPLE 1

The procedure of Example 1 was repeated except that a 0.5% aqueous ammonia was employed instead of 81.5 parts of an aqueous solution of sodium lactate, to give a uniform aqueous solution of carboxymethyl ethyl cellulose.

The solution had a MFT of not more than 25° C., and formed a transparent uniform film at temperatures higher the the MFT. The solution was coated onto tablets in the same manner as in Example 1, and the coated tablets were subjected to the disintegration test. In the test with the first fluid, cracks were generated at a portion of the tablet about 40 minutes later. Thus, the coating film was insufficient in the first fluid resistance.

COMPARATIVE EXAMPLE 2

The enteric coated tablets obtained in Example 1 were treated to remove sodium by immersing in 3 liters of 6N hydrochloric acid at 25° C. for 30 minutes and washing with running water until the washings no longer showed a red color with methyl orange indicator. The washed tablets were dried at 60° C. for 5 hours in an air oven, and then subjected to the disintegration test. In the test with the first fluid, cracks were generated at a portion of the tablet about 110 minutes later. The first fluid resistance was higher than that of the film obtained in Comparative Example 1, but was still insufficient.

COMPARATIVE EXAMPLE 3

A white aqueous dispersion of hydroxymethyl propyl cellulose phthalate was prepared in the same manner as in Example 6 except that 81.5 parts of water was employed instead of 81.5 parts of an aqueous solution of sodium citrate. The dispersion had a MFT of not less than 80° C., and did not form a continuous film at temperatures lower than 80° C. due to whitening.

In addition to the ingredients used in the Examples, other ingredients can be used in the Examples as set forth in the specification to obtain substantially the same results.

What we claim is:

1. An enteric coating liquid comprising an alkali metal salt of an acid having an acid dissociation constant (pKa) of at least 3 at 25° C. and a water-insoluble oxycarboxylic acid type cellulose derivative dispersed in water or a mixture of water and at most 20% by weight of a lower alcohol having 1 to 3 carbon atoms, said water-insoluble oxycarboxylic acid type cellulose derivative being derived from cellulose or a hydroxyalkyl cellulose by replacing up to three hydroxyl groups per glucose unit skeleton with at least two kinds of substituents, at least one substituent being selected from the group consisting of a carboxyalkyl ether group of the formula: —$OC_nH_{2n}COOH$ and a half ester group based on a dicarboxylic acid, and at least one substituent being selected from the group consisting of an ether group of the formula: —$OC_nH_{2n+1}$ and an ester group of the formula: —OOCR, wherein the alkyl in the hydroxyalkyl cellulose is a $C_1$ to $C_5$ alkyl, n is an integer of 1 to 5 and R is a $C_1$ to $C_5$ alkyl or a higher fatty acid residue.

2. The enteric coating liquid of claim 1, wherein said water-insoluble oxycarboxylic acid type cellulose derivative is a carboxyalkyl methyl cellulose or carboxyalkyl ethyl cellulose wherein the alkyl is a $C_1$ to $C_5$ alkyl.

3. The enteric coating liquid of claim 1, wherein the content of said oxycarboxylic acid type cellulose derivative is from 5 to 30% by weight.

4. The enteric coating liquid of claim 1, wherein said alkali metal salt is included in an amount of at most 30% by weight based on the oxycarboxylic acid type cellulose derivative.

5. An enteric coated pharmaceutical obtained by treating a pharmaceutical with a continuous film formed from an aqueous dispersion containing as essential components an alkali metal salt of an acid having an acid dissociation constant (pKa) of at least 3 at 25° C. and a water-insoluble oxycarboxylic acid type cellulose derivative in water or a water-alcohol mixed solvent containing at most 20% by weight of alcohol, said water-insoluble oxycarboxylic acid type cellulose derivative being derived from cellulose or a hydroxyalkyl cellulose by replacing up to three hydroxyl groups per glucose unit skeleton with at least two kinds of substituents, at least one substituent being selected from the group consisting of a carboxyalkyl ether group of the formula: —$OC_nH_{2n}COOH$ and a half ester group based on a dicarboxylic acid, and at least one substituent being selected from the group consisting of an ether group of the formula: —$OC_nH_{2n+1}$ and an ester group of the formula: —OOCR, wherein the alkyl in the hydroxyalkyl cellulose is a $C_1$ to $C_5$ alkyl, n is an integer of 1 to 5 and R is a $C_1$ to $C_5$ alkyl or a higher fatty acid residue.

* * * * *